United States Patent [19]

McCurdy

[11] Patent Number: 5,767,339
[45] Date of Patent: Jun. 16, 1998

US005767339A

[54] INBRED CORN LINE 85857

[75] Inventor: Leroy McCurdy, Freemont, Iowa

[73] Assignee: Mycogen Plant Science, Inc., San Diego, Calif.

[21] Appl. No.: 482,033

[22] Filed: Jun. 7, 1995

[51] Int. Cl.[6] .............................. A01H 5/00; A01H 4/00; A01H 1/00; C12N 5/04
[52] U.S. Cl. .............. 800/200; 800/250; 800/DIG. 56; 47/58; 47/DIG. 1; 435/412; 435/424; 435/430; 435/430.1
[58] Field of Search ........................... 800/200, 205, 800/250, DIG. 56; 47/58; 438/172.1; 435/412, 424, 430, 430.1

[56] References Cited

U.S. PATENT DOCUMENTS 5,285,003  2/1994  Harper, II ........................... 800/200

OTHER PUBLICATIONS

Phillips et al. "Cell/Tissue cultre and in vitro manipulation". COrn and Corn Improvement, 3rd ed. ASA Publication No. 18. p. 358. 1988.

*Primary Examiner*—Gary Benzion
*Attorney, Agent, or Firm*—Saliwanchik. Lloyd & Saliwanchik

[57] ABSTRACT

According to the invention, there is provided an inbred corn line designated 85857. Further provided are the plants and seeds of inbred corn line 85857, and hybrids produced using 85857 inbred line as one parent crossed with a distinct inbred corn line.

9 Claims, No Drawings

INBRED CORN LINE 85857

FIELD OF THE INVENTION

This invention relates to the field of corn breeding, and, more particularly, relates to an inbred corn line useful for creating high quality hybrid corn.

BACKGROUND OF THE INVENTION

The commercial value of field corn as a source of food and other products owes in large part to the development of hybrid seed. Virtually all corn grown commercially in the United States is planted from hybrid seed. Hybrid corn is generally understood to be the first generation of a cross between inbred lines, which have been developed by controlled self-pollination continued for several generations.

Inbred corn lines have genetically pure or homozygous genotypes. They will generally have desirable agronomic characteristics and be relatively resistant to insect and disease attacks, but will usually display reduced vigor and yield. Provided that the inbred parent lines are not closely related, corn hybrids will generally exhibit heterosis or hybrid vigor, i.e., which includes, yield greater than expected from either parent inbred line.

Typically, a commercially valuable inbred corn line results from plants that have been self-pollinated and selected for type for many generations. The plants become homozygous at almost all gene loci. Meiosis yields gametes of uniform genotype, and they produce a uniform population of true breeding progeny. A cross between two homozygous, inbred parent lines, each line producing uniform gametes, produces a uniform population of hybrid plants that may be heterozygous for many gene loci.

The development of high yielding corn hybrids that are agronomically sound based on stable inbred lines involves three steps: (1) the selection of plants from various germplasm pools; (2) the selfing of the selected plants for several generations to produce a series of parent inbred lines, each, although distinct from the others, breeding true and highly uniform; and (3) crossing the selected parent inbred lines with unrelated parent inbred lines to produce the hybrid progeny ($F_1$).

During the inbreeding process in corn, the vigor of the line decreases. Vigor is restored when two unrelated inbred lines are crossed to produce the hybrid progeny ($F_1$). An important consequence of the homozygosity and homogeneity of the parent inbred lines is that the hybrid between any two parent inbred lines will always be substantially the same. Once the parent inbred lines that give a superior hybrid have been identified, the hybrid seed can be reproduced indefinitely as long as the homogeneity of the inbred parent lines is maintained.

The breeder develops superior, inbred parental lines for producing hybrids by identifying and selecting in the progeny of diverse parents rare individuals having a desired phenotype or combination of traits based on a unique genetic endowment, which the breeder attempts to preserve by controlled inbreeding.

SUMMARY OF THE INVENTION

The present invention provides a novel inbred *Zea mays* L. corn line, designated 85857, adapted for a wide general combining ability. Also provided in the present invention are seeds of inbred corn line 85857 and the plants produced from seeds of inbred corn line 85857.

The invention further provides for hybrid corn plants produced from a cross between 85857 and a distinct second inbred *Zea mays* L. corn line. Also provided are tissue cultures of regenerable cells of the corn plant grown from 85857 seed as well as tissue cultures of regenerable cells of the hybrid corn plants produced from a cross between 85857 and a distinct second inbred *Zea mays* L. corn line.

DEFINITIONS

As used herein, the following definitions are provided:

| | |
|---|---|
| Apr | Appearance rating, which is a visual rating scaled from 1–5 of plant appearance on a plot basis; the lower the rating, the better the plant appearance. Appearance rating is equivalent to stay green, which is a measure of plant health at harvest. |
| Drop ear | Refers to dropped ears, which is a measure of the number of dropped ears per plot, and represents the percentage of plants for which ears were lost prior to harvest. |
| Ear ht | Refers to ear height, which is a measure in inches from the ground to the top developed ear node attachment. |
| Er | Refers to emergence rating, which is a visual rating scaled from 1–5 of seedling vigor on a plot basis; the lower the rating, the better the seedling vigor. |
| Kernel % >18.5 | Refers to the percentage of harvested grain that is larger than an 18½ round screen. |
| Kernel % 18.5–16.5 | Refers to the percentage of harvested grain that is smaller than an 18½ round screen, but larger than a 16½ round screen. |
| Kernel % <16.5 | Refers to the percentage of harvested grain that is smaller than a 16½ round screen; this portion of harvested seed is usually discarded as too small for planting. |
| Pop | Refers to population tested. The number given is the number in thousands of plants when converted to an acre basis. |
| Pt Ht | Refers to plant height, which is a measure of the height of the plant from the ground to the tip of the tassel in inches. |
| Root Lodg | Refers to root lodging, which is the percentage of plants that root lodge, i.e. plants that lean from the vertical axis at an approximately 30° angle or greater would be counted as root lodged. |
| Stlk Lodg | Refers to stalk lodging, which is the percentage of plants that stalk lodge (stalk breakage), as measured by natural lodging of the stalks. It is determined by counting the number of plants that have broken over below the ear. |
| Tst Wt | Refers to test weight, which is the pound of grain contained in a unit volume (bushel). |
| YLD | Refers to yield, which is the bushels of grain harvested per acre, converted to 15.5% moisture. |
| Y/M | Refers to yield/percent moisture; the higher this index, the more commercially valuable is the corn. |
| % MST | Refers to percent moisture, which is the actual moisture of the grain at harvest. |
| Susc. | Means susceptible. |
| Res. | Means resistant. |
| Selection | Occurs when plants with desired phenotypes or genotypes are chosen for additional plant breeding procedures and breeding projects. |
| Variety | A term used interchangeably with "cultivar" to denote a group of plants within a species, such as *Zea mays* L., which share certain stable characteristics that separate them from other possible varieties within that species. While possessing at least one distinctive trait, a variety can also be characterized by a substantial amount of variation between individuals within the variety, based primarily on the Mendelian segregation of traits among the progeny of succeeding generations. |
| Line | A line, as distinguished from "variety" and "cultivar," refers to a group of plants which are substantially uniform in their traits such that there is relatively minor variation within the group and such variation can be characterized. The decreased variation within this group has generally (although not exclusively) resulted from several generations of self pollination (selfing). |
| Heritable | A trait in a line or variety is considered heritable where the trait is genetically determined to the extent that when the line is crossed with a distinct line, the trait is passed on to the progeny. The trait is therefore considered heritable as it can be conferred upon hybrids which have |

|  |  |
|---|---|
| -continued | |
| True Breeding | the line as one of their parental antecedents. A line or variety is considered true breeding for a particular trait where it is genetically homozygous for that trait to the extent that when the line is self-pollinated, no significant amount of independent segregation of the trait among progeny is observed. The trait is then considered "fixed." This may also be defined in terms of whether the progeny show any significant variation with regard to the particular trait; if there is no significant variation, then the line is true breeding. |
| Commercially Acceptable Variety | Any variety, including inbreds and hybrids, which yields plants having agronomically acceptable traits. Such traits may relate to desirable factors such as high yield, a fast rate of dry-down, low stalk lodging, low root lodging, disease resistance, insect resistance, and the like, such that (a) with respect to inbreds, these traits allow the economical use of this genotype in the production of hybrid seed, or (b) with respect to hybrids, the acceptable traits are present in the hybrid plants when grown in a farmer's field. |

DETAILED DESCRIPTION OF THE INVENTION

Inbred Zea mays L. corn line 85857 is a yellow, dent corn inbred with superior characteristics and provides an excellent female parental inbred line yielding gametes of uniform genotype for crossing preferably with a variety or cultivar of Zea mays L. to produce first generation $F_1$ corn hybrids. The 85857 inbred line is best adapted over the Central cornbelt of the U.S.A but can be grown in the Northern and Central regions of the United States and Southern Canada (Ontario). The 85857 parent inbred line can be used to produce commercially acceptable varieties of hybrids from approximately 95–120 relative maturity based on the Minnesota Relative Maturity Rating System for harvesting moisture of grain. Because of its excellent yielding ability and good sizing, the 85857 parent inbred line is best used as a female parent.

The 85857 inbred line has shown uniformity and stability within the limits of environmental influence for the traits as described in the Variety Description Information (Table 1) that follows. Such uniformity and stability demonstrates that the 85857 parent inbred line produces gametes of uniform genotype. Table 1 compares the traits of corn plants grown from 85857 inbred line seed to those for inbred corn line B73, a publicly available inbred line (released from Iowa State University) which served as one parent in the development of the parent inbred line 85857. Most of the data in Table 1 was collected at York, Nebr. Inbred corn line 85857 exhibits a good late season plant health and has slight resistance to European corn borer.

The inbred line 85857 has been self-pollinated and ear-rowed for a sufficient number of generations with careful attention paid to selecting uniformity of plant type to ensure homozygosity and phenotypic stability. The homozygosity and phenotypic stability of the 85857 inbred line are maintained by the claimed inbred line's production of gametes having a uniform genotype. The claimed 85857 inbred line has been increased both by hand and in isolated fields with continued observation for uniformity. No variant traits have been observed or are expected in the 85857 inbred line.

Inbred corn line 85857, being substantially homozygous, can be reproduced by planting seeds of the 85857 inbred line and growing the resulting corn plants under self-pollinating or sib-pollinating conditions with adequate isolation. The resulting seed is harvested using techniques familiar to the agricultural arts.

The present invention provides hybrid corn plants produced from a cross between the 85857 parent inbred line and a second inbred Zea mays L. corn line sufficiently unrelated so that a hybrid created between the two inbred lines will exhibit heterosis, i.e., increased vigor and yield. All plants produced using parent inbred corn line 85857 as a parent in crosses with a cultivar of Zea mays L. are within the scope of this invention. The 85857 parent inbred line is used in crosses with other distinct parent Zea mays L. corn inbred lines to yield $F_1$, corn hybrid seeds and $F_1$ plants exhibiting heterosis, i.e. superior characteristics (a commercially acceptable variety).

A preferred embodiment of the subject invention is the $F_1$ hybrid resulting from the cross of the 85857 parent line with another inbred which has been transformed such that its genome comprises a gene derived from a Bacillus thuringiensis and encoding an insecticidal protein. Ideally, the gene will have been modified in accord with the teachings of U.S. Pat. No. 5,380,831, issued Jan. 10, 1995 to Adang et al., to optimize its level of expression. The $F_1$ hybrids resulting from this cross display heterosis and insect resistance.

As used herein, the term "plants and plant parts" includes plant cells, plant protoplasts, plant cell tissue culture from which corn plants can be regenerated, plant calli, plant clumps, and plant cells that are intact in plants or parts of plants, such as embryos, pollen, flowers, kernels, ears, cobs, leaves, husks, stalks, roots, root tips, anthers, silk and the like.

Regeneration of plants and plant parts from a parent inbred corn line or from a hybrid produced from a cross of two inbred corn lines is most common and in accordance with principles well-known in the art. Only in the most unusual circumstances is regeneration from a line impossible. In any given line, regenerable tissue culture is available from some part of the plant, making it possible to obtain regeneration of any line. While one may not be able to obtain regeneration from some parts of the corn plant, only in rare instances with present technology can one not obtain regeneration in any circumstances. Duncan et al (Planta (1985) 165:322–332) discloses that 97 percent of the hybrid cultures which produce callus are capable of plant regeneration. Subsequent experiments with both inbred lines and hybrids produced 91 percent regenerable callus, which regenerated plants. Songstad et al. (Plant Cell Reports (1988) 7:262–265) reported several media additions which enhanced regenerability of callus of two inbred lines. Other published reports also indicate that "nontraditional" tissues are capable of producing somatic embryogenesis and plant regeneration. K.V. Rao et al (Maize Genetics Cooperation Newsletter (1986) 60:64–65) refers to somatic embryogenesis from glume callus cultures, and B. V. Conger et al (Plant Cell Reports (1987) 6:345–347) indicates somatic embryogenesis from tissue cultures of maize leaf segments. Accordingly, one of ordinary skill in the art using conventional cell and tissue culture methods as referenced above is able to routinely obtain plants or plant parts with a high rate of success from regenerable cells of a tissue culture.

Tissue culture of corn is also described in European Patent Application, publication number 160,390, incorporated herein by reference. Corn tissue culture procedures are also described in Green and Rhodes, "Plant Regeneration in Tissue Culture of Maize," Maize for Biological Research (Plant Molecular Biology Association, Charlottesville, Va., 1982, pp. 367–372).

Accordingly, a further aspect of this invention provides cells which upon growth and differentiation produce the inbred line 85857. Further provided are cells which upon growth and differentiation produce a hybrid corn plant having a genotype derived from the fusion of a gamete produced by a 85857 inbred line plant and a gamete of the opposite sex produced by a second, inbred line of *Zea mays* L.

The seed of inbred corn line 85857, the plant produced from the inbred seed, the hybrid corn plant produced from the crossing of the claimed inbred, hybrid seed thereof, and various parts of the hybrid corn plant can be utilized for human food, livestock feed, and as raw material in industry.

EXAMPLES

The key characteristics and traits of the 85857 inbred line are presented in the data of Table 1. In Table 1, Applicant distinguishes the claimed 85857 inbred from the B73 inbred line, a commercially available inbred which served as one parent in the development of the 85857 inbred line. This table presents extensive morphological and physiological differences between the 85857 inbred line and the B73 inbred line.
Deposits Applicant makes available to the public without restriction a deposit of at least 2500 seeds of the 85857 inbred line with the American Type Culture Collection (ATCC), Rockville, Md. 20852. The deposit is designated as ATCC Deposit No. 209078. The seeds deposited have been maintained since prior to the filing date of the present application by Mycogen Plant Sciences, 5649 East Buckeye Road, Madison, Wis. 53716. The deposit of the inbred corn line 85857 without restriction will be maintained at the ATCC Depository, which is a public depository, for a period of 30 years, or five years after the most recent request, or for the effective life of the patent, whichever is longer, and will be replaced if it becomes nonviable during that period.

TABLE 1 - 85857

| Variety Description Information | | |
|---|---|---|
| CHARACTERISTIC | 85857 | B73 |
| Type | dent | dent |
| A. Seedling Stage | | |
| Seedling Vigor | high | high |
| Plant ht. at 7 leaf stage (cm) | 90 | 89 |
| Anthocyanin pigment at seedling stage | absent | low |
| B. Flowering Stage | | |
| Tassel length, central spike (cm) | 21 | 19 |
| Tassel length, side branches | 8.5 | 11 |
| Tassel angle | 25° | 30° |
| Number of tassel branches | 11 | 6 |
| Anther color | yellow | yellow |
| Glume color | green | purple |
| Fresh husk color | lt. green | lt. green |
| C. Leaves | | |
| Leaf angle | semi-erect | very erect |
| Leaf color | med. | med. |
| Leaf width (cm) | *7 | *6 |
| Anthocyanin at leaf blade borders | none | none |
| D. Stalk and Roots | | |
| Plant ht. to top of tassel (cm) | 220 | 230 |
| Plant length to top ear node (cm) | 109 | 102 |

TABLE 1 - 85857-continued

| Variety Description Information | | |
|---|---|---|
| CHARACTERISTIC | 85857 | B73 |
| Anthocyanin pigment of nodes | none | none |
| Anthocyanin pigment of internodes | none | low |
| E. Ear Traits | | |
| Cob color | red | pink |
| Cob diameter at midpoint (cm) | *3 | *5 |
| Ear diameter (cm) | 3 cm | 5.0 |
| Ear length (cm) | 10–15 cm | 15 cm |
| Ear shape | cylind. | cylind. |
| Husk length | *7 | *6 |
| Number of kernel rows | 20 | 18 |
| Straightness of kernel rows | spiral | straight |
| Uniformity (cob color, ear type) | uniform | uniform |
| F. Maturity | | |
| Days, emergence to 50% silking | 80 | 78 |
| Days, emergence to 50% pollen shed | 80 | 77 |
| G. Kernel (dry) | | |
| Size | | |
| a. length (mm) | 10 | 12 |
| b. width (mm) | 6.0 | 7.5 |
| c. thick (mm) | 3.0 | 3.0 |
| Pericarp color | yellowish | colorless |
| Aleurone color | colorless | variegated |
| Endosperm color | yellow | yellow |
| Endosperm type | normal | normal |
| H. Disease Resistance | | |
| Diplodia stalk rot | susc. | susc. |
| Fusarium stalk rot | susc. | susc. |
| Maize dwarf mosaic | susc. | susc. |
| I. Insect Resistance | | |
| Corn borer | slight | susc. |

[*=Description of components and varieties of Maize (FRASEMA)]

What is claimed is:

1. Inbred corn seed designated 85857, having ATCC accession number 209078.

2. A corn plant produced by the seed of claim 1.

3. A tissue culture of regenerable cells of the plant of claim 2.

4. A corn plant regenerated from the issue culture of claim 3 capable of expressing all the morphological and physiological properties of inbreed 85857 having ATCC number 209078.

5. An inbred corn plant having all the physiological and morphological characteristics of the corn plant of claim 2.

6. An F₁ hybrid corn plant having all a genome which comprises a gamete of inbred corn plant 85857, said inbred corn having ATCC accession number 209078.

7. Corn seed produced by the F₁ hybrid corn plant of claim 6.

8. Corn seed which is capable of producing a corn plant comprising a gamete of inbred corn plant 85857.

9. A tissue culture of regenerable cells of the plant of claim 6.

* * * * *

UNITED STATES PATENT AND TRADEMARK OFFICE
CERTIFICATE OF CORRECTION

PATENT NO. : 5,767,339

DATED : June 16, 1998

INVENTOR(S) : Leroy McCurdy

It is certified that error appears in the above-identified patent and that said Letters Patent is hereby corrected as shown below:

Column 4, line 19: "et aL.," should read --et al.,-- ;

line 39: "et al" should read --*et al.*--;

line 49: "et al" should read --*et al.*--; and line 51: "et al" should read --*et al.*--.

Column 6, line 51 (Claim 6): "having all a genome" should read --having a genome--.

Signed and Sealed this

Twenty-second Day of September, 1998

Attest:

BRUCE LEHMAN

*Attesting Officer*     *Commissioner of Patents and Trademarks*